United States Patent
Ivri

[11] Patent Number: 5,938,117
[45] Date of Patent: *Aug. 17, 1999

[54] METHODS AND APPARATUS FOR DISPENSING LIQUIDS AS AN ATOMIZED SPRAY

[75] Inventor: Yehuda Ivri, Palo Alto, Calif.

[73] Assignee: Aerogen, Inc., Sunnyvale, Calif.

[*] Notice: This patent is subject to a terminal disclaimer.

[21] Appl. No.: 08/417,311

[22] Filed: Apr. 5, 1995

Related U.S. Application Data

[63] Continuation-in-part of application No. 08/163,850, Dec. 7, 1993, which is a continuation-in-part of application No. 07/726,777, Jul. 8, 1991, abandoned, which is a continuation-in-part of application No. 07/691,584, Apr. 24, 1991, Pat. No. 5,164,740.

[51] Int. Cl.⁶ .......................... G01D 15/16; G01D 15/18
[52] U.S. Cl. ...................... 239/4; 239/102.2; 346/140.1; 346/141; 347/47; 347/70
[58] Field of Search .............................. 239/102.2, 102.1, 239/4; 346/140.1, 141; 347/6, 9, 20, 47, 68, 70

[56] References Cited

U.S. PATENT DOCUMENTS

| | | |
|---|---|---|
| 2,101,304 | 12/1937 | Wright . |
| 2,158,615 | 5/1939 | Wright . |

(List continued on next page.)

FOREIGN PATENT DOCUMENTS

| | | |
|---|---|---|
| 0 049 636 A1 | 4/1982 | European Pat. Off. . |
| 0 103 161 A2 | 3/1984 | European Pat. Off. . |
| 0 134 847 A1 | 3/1985 | European Pat. Off. . |
| 0 542 723 A2 | 5/1993 | European Pat. Off. . |
| 57-23852 | 2/1982 | Japan . |
| 57-105608 | 7/1982 | Japan . |
| 58-61857 | 4/1983 | Japan . |
| 58-139757 | 8/1983 | Japan . |
| 60-4714 | 1/1985 | Japan . |
| 61-8357 | 1/1986 | Japan . |
| 61-215059 | 9/1986 | Japan . |
| 2-135169 | 5/1990 | Japan . |
| 2-189161 | 7/1990 | Japan . |
| 973458 | 10/1964 | United Kingdom . |
| 1454597 | 11/1976 | United Kingdom . |
| 2 073 616 | 10/1981 | United Kingdom . |
| 2 177 623 | 1/1987 | United Kingdom . |
| 2 240 494 | 8/1991 | United Kingdom . |
| 2 272 389 | 5/1994 | United Kingdom . |
| WO 92/11050 | 7/1992 | WIPO . |
| WO 93/01404 | 1/1993 | WIPO . |

OTHER PUBLICATIONS

Berglund, R.N., et al. Generation of Monodisperse Aerosol Standards. Environ. Sci. Technology 7:2:147 (1973).

Allen, T. Particle Size Measurement. Chapman and Hall pp. 167–169 (1981).

Ueha, S., et al. Mechanism of Ultrasonic Atomization Using a Multi–Pinhole Plate. J. Acoust. Soc. Jpn. (E)6,1:21 (1985).

Maehara, N., et al. Influence of the Vibrating System of a Multipinhole–plate Ultrasonic Nebulizer on Its Performance. Review of Scientific Instruments, 57 (11), Nov. 1986, pp. 2870–2876.

(List continued on next page.)

*Primary Examiner*—Andres Kashnikow
*Attorney, Agent, or Firm*—Townsend and Townsend and Crew

[57] ABSTRACT

The invention provides exemplary methods and apparatus for dispensing liquids as an atomized spray. In one particularly preferably method, a liquid is dispensed as an atomized spray from a vibratable member having a front surface and a rear surface, with the member having at least one tapered hole between the surfaces for dispensing the liquid. The tapered hole has a larger cross-sectional area at the rear surface than at the front surface. The liquid is delivered from a supply container to the rear surface of the vibratable member in an amount sufficient to cover the hole with liquid. The vibratable member is then vibrated to dispense at least a portion of the liquid through the hole and from the front surface. Additional liquid is delivered from the supply container and to the rear surface in volumes that are substantially equal to the volumes dispensed.

31 Claims, 11 Drawing Sheets

U.S. PATENT DOCUMENTS

| | | |
|---|---|---|
| 2,187,528 | 1/1940 | Wing . |
| 2,223,541 | 12/1940 | Baker . |
| 2,283,333 | 5/1942 | Martin . |
| 2,292,381 | 8/1942 | Klagges . |
| 2,360,297 | 10/1944 | Wing . |
| 2,375,770 | 5/1945 | Dahlberg . |
| 2,404,063 | 7/1946 | Healy . |
| 2,430,023 | 11/1947 | Longmaid . |
| 2,474,996 | 7/1949 | Wallis . |
| 2,512,004 | 6/1950 | Wing . |
| 2,521,657 | 9/1950 | Severy . |
| 2,681,041 | 6/1954 | Zodtner et al. . |
| 2,779,623 | 3/1957 | Eisenkraft . |
| 2,935,970 | 5/1960 | Morse et al. . |
| 3,411,854 | 11/1968 | Rösler et al. . |
| 3,558,052 | 1/1971 | Dunn . |
| 3,738,574 | 6/1973 | Guntersdorfer et al. . |
| 3,790,079 | 2/1974 | Berglund et al. . |
| 3,804,329 | 4/1974 | Martner . |
| 3,812,854 | 5/1974 | Michaels et al. . |
| 3,950,760 | 4/1976 | Ilse-dore Stromberger et al. . |
| 3,958,249 | 5/1976 | DeMaine et al. . |
| 3,983,740 | 10/1976 | Danel . |
| 4,005,435 | 1/1977 | Lundquist et al. . |
| 4,159,803 | 7/1979 | Cameto et al. . |
| 4,240,081 | 12/1980 | Devitt . |
| 4,261,512 | 4/1981 | Zierenberg . |
| 4,294,407 | 10/1981 | Reichl et al. . |
| 4,300,546 | 11/1981 | Kruber . |
| 4,334,531 | 6/1982 | Reichl et al. . |
| 4,336,544 | 6/1982 | Donald et al. . |
| 4,338,576 | 7/1982 | Takahashi et al. . |
| 4,368,476 | 1/1983 | Uehara et al. . |
| 4,389,071 | 6/1983 | Johnson, Jr. et al. . |
| 4,408,719 | 10/1983 | Last . |
| 4,431,136 | 2/1984 | Janner et al. . |
| 4,465,234 | 8/1984 | Maehara et al. . |
| 4,474,251 | 10/1984 | Johnson, Jr. . |
| 4,474,326 | 10/1984 | Takahashi . |
| 4,475,113 | 10/1984 | Lee et al. . |
| 4,479,609 | 10/1984 | Maeda et al. . |
| 4,530,464 | 7/1985 | Yamamoto et al. . |
| 4,533,082 | 8/1985 | Maehara et al. . |
| 4,539,575 | 9/1985 | Nilsson . |
| 4,544,933 | 10/1985 | Heinzl . |
| 4,546,361 | 10/1985 | Brescia et al. . |
| 4,550,325 | 10/1985 | Viola . |
| 4,591,883 | 5/1986 | Isayama . |
| 4,593,291 | 6/1986 | Howkins . |
| 4,605,167 | 8/1986 | Maehara . |
| 4,620,201 | 10/1986 | Heinzl et al. . |
| 4,628,890 | 12/1986 | Freeman . |
| 4,632,311 | 12/1986 | Nakane et al. . |
| 4,659,014 | 4/1987 | Soth et al. . |
| 4,681,264 | 7/1987 | Johnson, Jr. . |
| 4,702,418 | 10/1987 | Carter et al. . |
| 4,753,579 | 6/1988 | Murphy . |
| 4,790,479 | 12/1988 | Matsumoto et al. . |
| 4,793,339 | 12/1988 | Matsumoto et al. . |
| 4,796,807 | 1/1989 | Bendig et al. . |
| 4,799,622 | 1/1989 | Ishikawa et al. . |
| 4,828,886 | 5/1989 | Hieber . |
| 4,850,534 | 7/1989 | Takahashi et al. . |
| 4,865,006 | 9/1989 | Nogi et al. . |
| 4,888,516 | 12/1989 | Daeges et al. . |
| 5,021,701 | 6/1991 | Takahashi et al. . |
| 5,063,396 | 11/1991 | Shiokawa et al. . |
| 5,152,456 | 10/1992 | Ross et al. . |
| 5,164,740 | 11/1992 | Ivri . |
| 5,198,157 | 3/1993 | Bechet . |
| 5,261,601 | 11/1993 | Ross et al. . |
| 5,297,734 | 3/1994 | Toda . |
| 5,299,739 | 4/1994 | Takahashi et al. . |
| 5,518,179 | 5/1996 | Humberstone et al. . |

OTHER PUBLICATIONS

Maehara, N., et al. Optimum Design Procedure for Multi–Pinhole–Plate Ultrasonic Atomizer. Japanese Journal of Applied Physics, 26:215 (1987).

Ashgriz, N., et al. Development of a Controlled Spray Generator. Rev. Sci. Instrum. 58(7):1291 (1987).

Hikayama, H., et al. Ultrasonic Atomizer with Pump Function. Tech. Rpt. IEICE Japan US88–74:25 (1988).

J. Acoustical Soc. Japan 44:2:116 (1988).

J. Acoustical Soc. Japan 44:6:425 (1988).

Siemens AG, 1989, "Ink–Jet Printing: The Present State of the Art," by Wolfgang R. Wehl.

TSI Incorporated product catalog. Vibrating Orifice Aerosol Generator (1989).

Gaiser Tool Company catalog, pp. 26, 29–30 (19_).

Nogi, T., et al. Mixture Formation of Fuel Injection System in Gasoline Engine. Nippon Kikai Gakkai Zenkoku Taikai Koenkai Koen Ronbunshu 69:660 (1991).

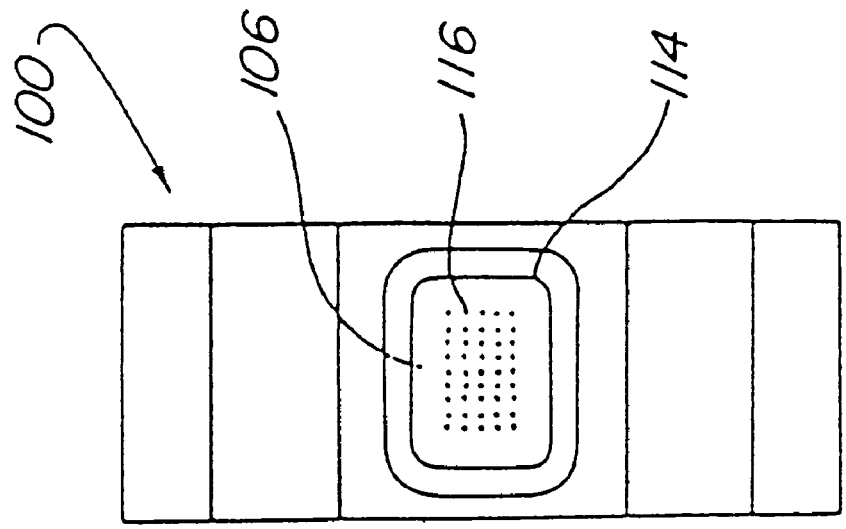
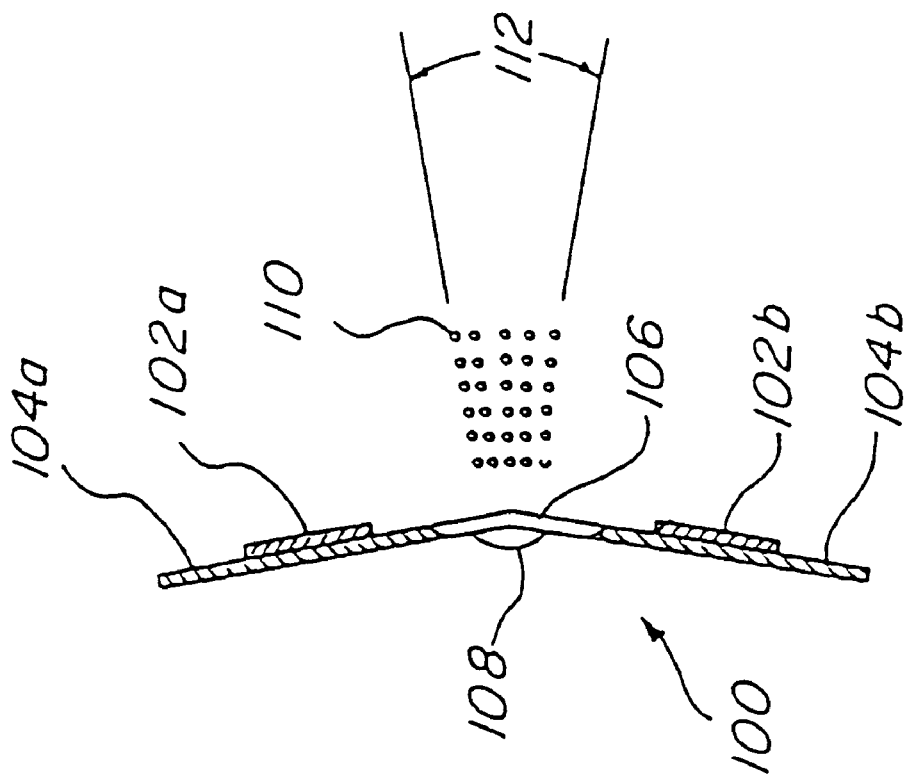

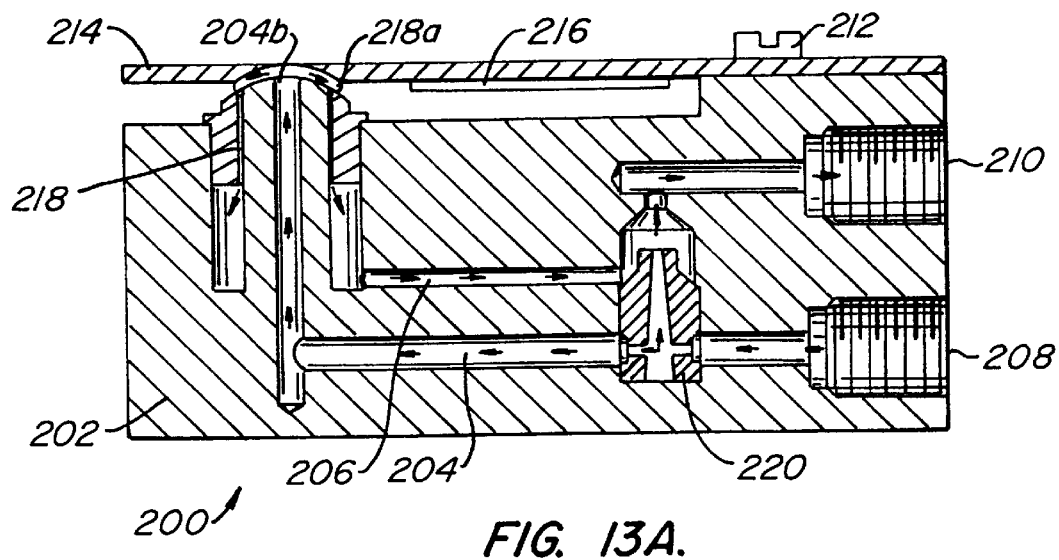
FIG. 13A.
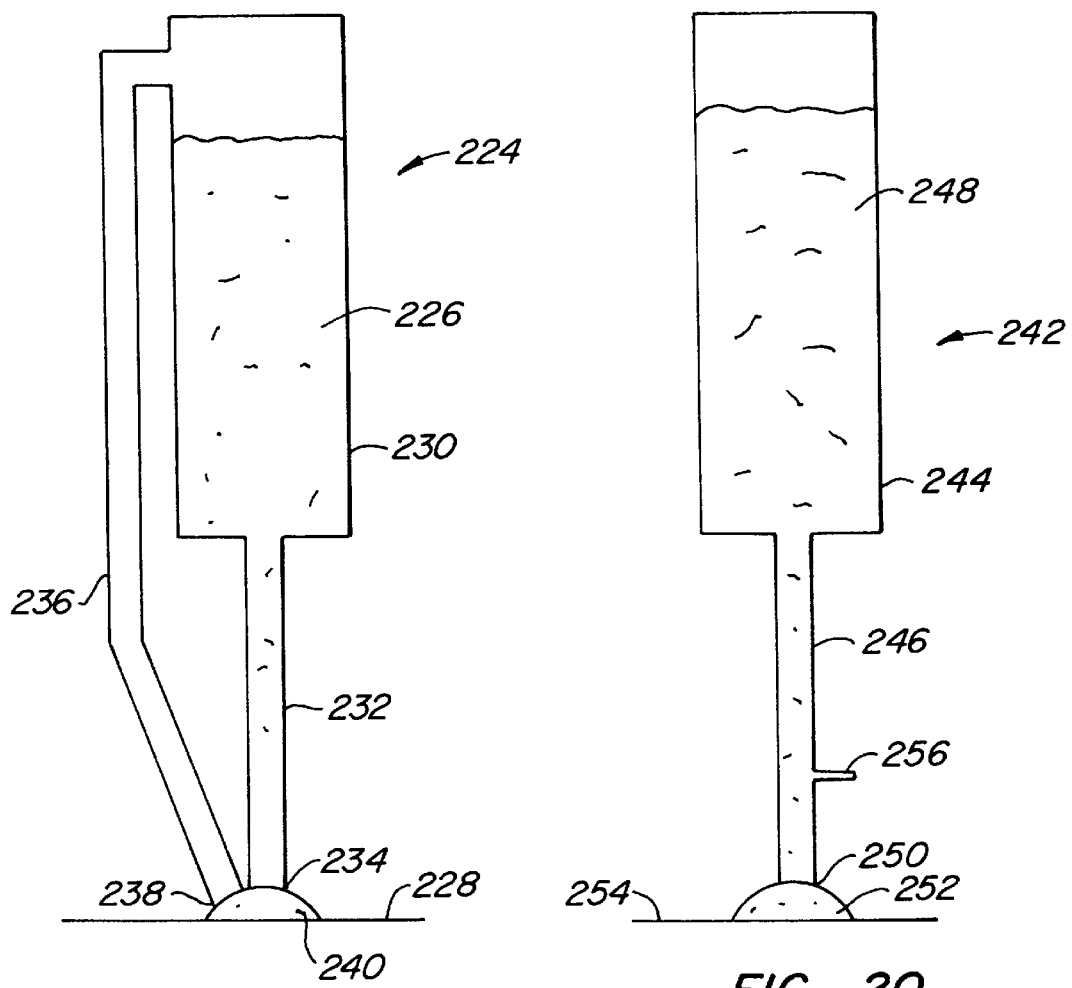
FIG. 19.
FIG. 20.

METHODS AND APPARATUS FOR DISPENSING LIQUIDS AS AN ATOMIZED SPRAY

CROSS-REFERENCE TO RELATED APPLICATIONS

This application is a continuation-in-part application of U.S. patent application Ser. No. 08/163,850, filed on Dec. 7, 1993, which is a continuation-in-part of U.S. patent application Ser. No. 07/726,777, filed on Jul. 8, 1991 (now abandoned), which is a continuation-in-part of U.S. patent application Ser. No. 07/691,584, filed on Apr. 24, 1991, now U.S. Pat. No. 5,164,740. The complete disclosures of all these applications are herein incorporated by reference.

BACKGROUND OF THE INVENTION

1. Field of the Invention

The present invention relates to the fields of liquid spray and atomization of liquids of all kinds and, more specifically, finds utility in humidification and misting, industrial cleaning, surface coating and treatment, particle coating and encapsulating, fuel atomization, deodorization, disbursement of insecticides, aerosols, and medical spray applications.

2. Description of Related Art

Many types of ultrasonic fluid ejection devices have been developed for atomizing of water or liquid fuel. These atomizers can be classified into two groups. The first type atomizes liquid that forms a thin layer on an ultrasonically-excited plate. The first type is not capable of ejecting atomized fluid droplets. U.S. Pat. No. 3,738,574 describes an atomizer of this type.

The second type utilizes a housing defining an enclosed chamber. The housing includes a perforated membrane or a pinhole membrane as the front wall of the chamber. The apparatus further includes a means to vibrate the membrane or a side wall of the chamber, typically by a piezoelectric element affixed to the front face of the chamber. The piezoelectric element oscillates the fluid in the chamber. As a result, pressure waves are generated in the chamber, forcing fluid through the open pinholes. All the devices of the second type require fluid to be kept inside the chamber next to the discharge opening. When volatile fluids are used, problems arise. The volatile fluids escape through the discharge opening. Hence, liquid may undesirably outflow from the opening. The discharge opening will clog, restricting or stopping further discharge. These problems are prevalent with volatile fluids such as fuel, paint, or other coating materials. To overcome at least some of these problems, U.S. Pat. No. 4,533,082 uses a vacuum pump to ensure that the liquid in the chamber is kept under negative pressure to prevent outflow.

Other variations of apparatus for ejecting atomized liquid, utilizing one of the above two types, are disclosed in U.S. Pat. Nos. 3,812,854, 4,159,803, 4,300,546, 4,334,531, 4,465,234, 4,632,311, 4,338,576, and 4,850,534.

Certain writing instruments, such as fountain pens, employ mechanisms for controlling the flow of ink from a supply container to the writing tip of the pen.

SUMMARY OF THE INVENTION

The present invention provides an ejection device that includes a free oscillating surface having microscopic tapered apertures of a selected conical cross-sectional shape. A layer of fluid adheres in surface tension contact with the oscillating surface. The apertures draw fluid into their large openings and eject the fluid from their small openings to a great distance. The ejection action is developed by the aperture, regardless of the amount of fluid in contact with the oscillating surface, and without any fluid pressure. Both sides of the oscillating surface are operating under the same ambient pressure. Therefore, the ejection device can operate equally well in vacuum or high-pressure environments. The supplied liquid continuously adheres to the large opening by surface tension. The film of fluid oscillates with the surface while it is being drawn into the large opening of the aperture and ejected forwardly. This continues until all the fluid is drawn from the surface, leaving the surface dry and free of liquid during the time that the device is not in use.

If the cross-section of the aperture is chosen with respect to the fluid to be ejected, the oscillation required to produce ejection is kept small, and the film of fluid on the oscillating surface appears to be dynamically at rest during ejection. By supplying only enough fluid to continuously form a thin film, in surface tension contact with the oscillating surface, to the side containing the large openings of the tapered apertures, neither clogging nor uncontrolled emission or leakage through the apertures occurs. The device can operate under any pressure conditions.

In an alternative embodiment, the invention provides an apparatus for dispensing liquids as an atomized spray. The apparatus preferably includes a vibratable member having a front surface, a rear surface, and at least one tapered hole extending therebetween. The tapered hole has a larger cross-sectional area at the rear surface than at the front surface. A means is provided for vibrating the member, and a supply container is provided for holding the liquid to be dispensed. A means is provided for delivering the liquid from the supply container and to the rear surface of the vibratable member. A flow regulator is further included for regulating the flow of the liquid from the container and to the vibratable member. The flow regulator is configured to allow delivery of the liquid to the rear surface in volumes that are substantially equal to the volumes dispensed from the vibratable member. Preferably, the liquid is delivered to the rear surface of the vibratable member at a rate that is substantially equal to the rate of the liquid being dispensed from the front surface. In this way, the flow of liquid from the supply container and to the rear surface is regulated so that neither insufficient nor excessive amounts of liquid are delivered to the rear surface. In this manner, an optimal amount of liquid is provided to the rear surface during operation of the apparatus.

In a preferable aspect, the flow regulator includes an air vent that is in fluid communication with the supply container. When open, the air vent allows air to flow into the supply container in volumes that are sufficient to replace the volumes that are delivered to the rear surface. In this way, delivery of liquid to the rear surface can be controlled by regulating the amount of air flowing to the supply container. Preferably, opening and closing of the air vent is controlled by the liquid itself as it travels from the supply container and to the rear surface. As liquid flows from the supply container, some of the liquid flows into and closes the air vent thereby preventing air from entering the supply container. As liquid continues to flow from the container, a vacuum is created in the container to prevent additional flow of liquid from the container. Upon ejection of liquid from the vibratable member, liquid in the air vent flows to the rear surface to replace the ejected liquid. In this way, the air vent is again opened to allow air to enter the container and to allow additional liquid to flow from the supply container.

In a further aspect, the supply container is preferably oriented in a position that facilitates the flow of liquid from the container and to the rear surface. In another aspect, the air vent is distanced from the supply container at a distance sufficient to allow the liquid to be delivered to the rear surface at a rate that is substantially equal to the rate of liquid dispensed from the hole.

The invention further provides a method for dispensing liquid droplets as an atomized spray, with the liquid being delivered from a supply container. According to the method, liquid is delivered from the supply container and to the rear surface of a vibratable member in an amount sufficient to cover a hole in the member with liquid. The liquid is held in the hole by surface tension. The vibratable member is then vibrated to dispense at least a portion of the liquid through the hole, with the liquid being dispensed from a front surface of the member. Additional liquid is delivered from the supply container and to the rear surface in volumes that are held in surface tension contact to the rear surface of the vibratable member, i.e. the entire volume of liquid that is delivered to the rear surface is held to the rear surface by surface tension forces so that the delivered liquid will remain attached to the rear surface until ejected. Preferably, the liquid is delivered to the rear surface at a rate that is substantially equal to the rate of the liquid being dispensed from the front surface.

In an exemplary aspect, preselected volumes of air are exchanged with liquid from the supply container to deliver the additional volumes of liquid to the rear surface. Preferably, the preselected volumes of air are sufficient to replace the volumes of liquid that are delivered from the supply container and to the rear surface. In this way, by controlling the supply of air volumes to the supply container, the amount of liquid delivered to the rear surface can be regulated. Preferably, the supply of air to the supply container is controlled by opening and closing an air vent that is in communication with the supply container. In one aspect, the air vent is closed upon filling of the air vent with liquid from the supply container as the liquid flows toward the rear surface of the vibratable member. As liquid is ejected from the vibratable member, liquid flows from the air vent and to the rear surface to replace the ejected liquid, thereby opening the air vent and allowing air to flow into the supply container. In turn, the air supplied to the container allows additional liquid to flow from the supply container and the process is repeated until vibration of the member is ceased.

The rate of liquid dispensed from the vibratable member can widely vary depending on the number of apertures and the size of each aperture. In one particular aspect which is not meant to be limiting, the liquid is an insecticide which is dispensed at a rate in the range of approximately 0.1 cm$^3$ to 10 cm$^3$ per hour, and more preferably at about 0.5 cm$^3$ to 2 cm$^3$ per hour. Preferably, the insecticide is ejected from the front surface in droplets having a mean size in the range from 1 $\mu$m to 15 $\mu$m, and more preferably at about 3 $\mu$m to 10 $\mu$m. In another aspect which is not meant to be limiting, the liquid is a deodorant, usually an air freshener, which is dispensed at a rate of approximately 0.1 cm$^3$ to 10 cm$^3$ per hour, and more preferably at about 1 cm$^3$ to 2 cm$^3$ per hour. Preferably, the deodorant is ejected from the front surface in droplets having a size in the range from 1 $\mu$m to 15 $\mu$m, and more preferably at about 3 $\mu$m to 10 $\mu$m.

In another embodiment of the invention, an apparatus which is particularly useful as an insecticizer or a deodorizer is provided. The apparatus includes a housing having at least one ejection port and a vibratable member within the housing. The vibratable member includes a tapered hole that is aligned with the ejection port. A means is provided for supplying liquid to a rear surface of the vibratable member, and a means is provided in the housing for vibrating the member. The housing is conveniently configured to receive a liquid supply container for holding a deodorant or an insecticide. When connected to the supply container, the apparatus can be placed at a strategic location and actuated to dispense the liquid. In a preferable aspect, a battery is employed as a power source to vibrate the member, thereby allowing the apparatus to be placed in a variety of locations and to be left unattended while dispensing liquid.

In another exemplary aspect, the apparatus is provided with a controller for controlling actuation of the vibratable member. Preferably, the controller is preprogrammed to cyclically actuate the vibratable member according to a preselected ejection schedule. Such a configuration is particularly useful when dispensing an insecticide which requires careful control of the amount of insecticide that is dispensed into the atmosphere. In another preferable aspect, upon depletion of the liquid from the supply container, a refill supply container can be attached to the housing and the apparatus reused. In still a further aspect, the refill container is provided with a pair of N size cell batteries which serve as the power source to vibrate the member. The batteries are provided with sufficient energy to eject the full content of the refill.

BRIEF DESCRIPTION OF THE DRAWINGS

The general purpose and advances of the present invention will be more fully understood hereinafter as a result of the detailed description of the preferred embodiments when taken in conjunction with the following drawings, in which:

FIG. 13A illustrates a further alternative apparatus for preventing accidental overflow in a fluid supply system.

FIG. 17 is a side view of another alternative preferred embodiment of the fluid ejection device according to the present invention.

FIG. 18 is a front view of the fluid ejection device of FIG. 17.

FIG. 19 is a schematic view of an apparatus for controlling delivery of a liquid from a supply container.

FIG. 20 is a schematic view of an alternative apparatus for controlling delivery of a liquid from a supply container.

INTRODUCTION

Figure 1:
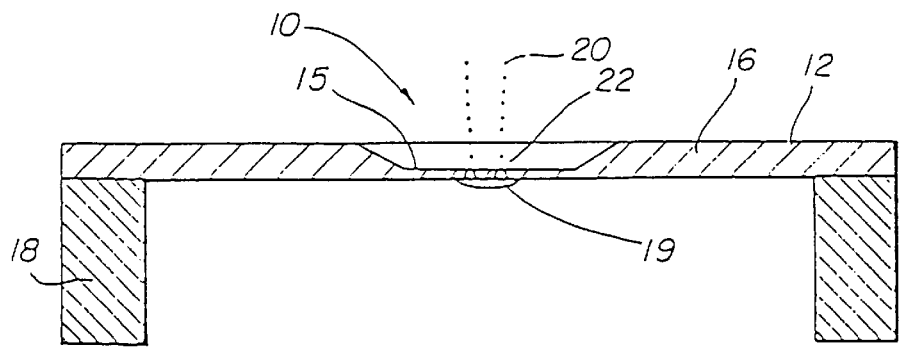
FIG. 1 is a schematic illustration of a preferred embodiment of a device according to the present invention.

The present invention provides a new fluid ejection device that is especially advantageous in applications that require ejection of fluid droplets without fluid pressure and without a propellant and in ambient pressure environments.

A particularly important application for the present invention is industrial spray systems. The ejector is capable of ejecting viscose liquid such as paint and coating materials without the use of compressed air.

The use of air as a propellant in paint spray application causes overspray, in that part of the paint droplets escape to the atmosphere and cause air pollution. The transfer efficiency, that is, the percentage amount of coating material, such as paint, that reaches the target, is significantly increased when ejection is without air.

Another important application of the present invention is for consumer products such as deodorant and hair spray. The use of propellants in conventional aerosols, commonly known as volatile organic chemicals (VOCs), has a negative effect on the environment and on human health. There is an ongoing trend to find ways to atomize fluid without using such propellant gases.

The present invention provides a device that ejects fluid from microscopic tapered apertures. The fluid is transported to the ejecting surface at the large opening of the tapered aperture. A cohesive attraction force (surface tension) exclusively causes the liquid to adhere to the tapered aperture. The solid/fluid interaction of the fluid with the tapered aperture wall causes fluid to be drawn into the large opening of the aperture and ejected from its small opening. This ejection action is attributed to the geometry of the aperture, as well as the fluid characteristics such as viscosity, density, and elasticity. The fluid supply to the surface is tightly controlled to prevent overflow of liquid from the supply side of the oscillating surface. A flow control valve or a two-way valve is provided to control the amount of fluid that is transported to the surface. The valve may have a built-in electrical contact that activates oscillation simultaneously with the flow of fluid.

During ejection, fluid is supplied to the oscillating surface from a discharge nozzle that is in close proximity to the oscillating surface. The fluid is held by surface tension forces in the small gap between the front face of the fluid supply nozzle and the oscillating surface. When the fluid supply is stopped, the surface with the tapered apertures is allowed to oscillate for a period of time sufficient for the apertures to draw all the fluid from the oscillating surface and the gap. When not in use, the gap, as well as the oscillating surface and the aperture, remain free of fluid.

The discharge nozzle is preferably made of elastomer material having a cut through its thickness. The cut is normally closed due to the elasticity of the elastomer. The cut opens under slight pressure when fluid is transported from the supply container. This arrangement keeps the fluid in the container hermetically sealed during periods of non-use.

An electronic wave generator with a circuit that can turn the oscillating action on and off sequentially at a very high speed is preferred. The ratio of the "on" period versus the "off" period controls the duty cycle of ejection and, therefore, the ejection mean flow rate. Maximum flow is achieved when the oscillator is continuously "on".

Fluid is preferably supplied to the oscillating surface at a rate that is lower than the maximum ejection rate of the aperture. If the fluid supply exceeds the maximum ejection rate of the apertures, excessive fluid may overflow from the supply side of the oscillating surface. When the fluid used is paint or ink, overflow is undesirable. To prevent overflow, a system to collect liquid overflow may be used. This system includes a ring provided with a slot at its circumference which is connected to a pump. If fluid accidentally escapes from the oscillating surface and reaches the slot, it is drawn and returned to the supply container.

Another method of preventing accidental overflow is provided by an electronic flow control valve. It has been found that as the amount of liquid over the surface increases, the current draw by the piezoelectric element decreases. If the current draw reaches a predetermined level which indicates that an overflow is about to occur, the electronic circuit transmits a signal to the flow control valve to reduce the flow of liquid to the surface. Thereby, overflow is avoided.

A further method of preventing accidental overflow is provided by a flow regulator that regulates the flow of liquid from a supply container to the oscillating surface. The flow regulator includes an air vent that is in communication with the supply container. By closing the air vent, air is prevented from entering the supply container which in turn creates a vacuum in the container to prevent liquid from flowing from the container. By having at least some of the liquid within the container configured to flow into the air vent, operation of the air vent can be controlled by the liquid itself as it travels to the oscillating surface. As liquid is dispensed by the oscillating surface, liquid is drained from the air vent and flows to the oscillating surface to open the air vent and allow air into the container. In this manner, air enters into the supply container in volumes that are substantially equal to liquid volumes dispensed from the oscillating surface and at a rate substantially equal to the rate of ejection. Such a configuration allows for an optimal amount of liquid to automatically be delivered to the oscillating surface upon operation of the device.

DETAILED DESCRIPTION OF THE SPECIFIC EMBODIMENTS

Referring now to FIG. 1, it will be seen that the fluid ejection device 10 of the present invention comprises a vibrating surface 12 having a perimeter area 14 and a center area 16. The perimeter 14 of vibrating surface 12 is affixed to an oscillator 18 which may, for example, be piezoceramic. The center area 16 of vibrating surface 12 is provided with a planar surface 15 through which there are apertures 22. The portion of center 15 having the apertures is in surface tension contact with a fluid film 19 at the back side of planar surface 15 to produce an ejection of fluid droplets 20.

Figure 2:
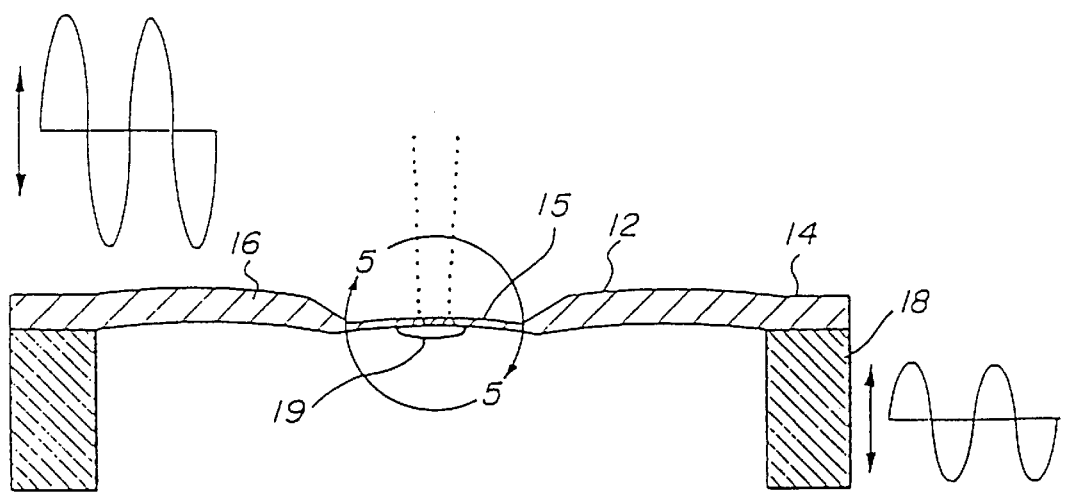
FIG. 2 is the schematic illustration of the present invention of FIG. 1 shown in its oscillating configuration.

The oscillatory motion of the vibrating surface 12 is shown in FIG. 2. It will be seen therein that the perimeter 14 of the vibrating surface 12, by virtue of its contact with the oscillator 18, oscillates in a vertical direction, as viewed in FIG. 2, with an oscillating characteristic shown in the graph at the rightmost portion of FIG. 2. As also seen in FIG. 2, the center 16 of vibrating surface 12 oscillates at the same frequency as the perimeter 14, but with a much larger amplitude, as seen in the graph on the leftmost portion of FIG. 2. The graphs of FIG. 2 are for purposes of illustration and are not necessarily drawn to scale.

Figure 3:
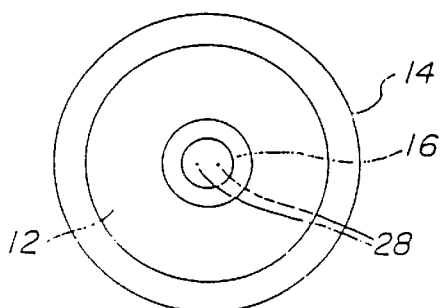
FIG. 3 is a top view of a vibrating surface according to the present invention.
Figure 4:
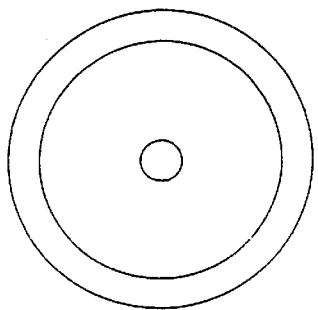
FIG. 4 is a bottom view of a vibrating surface according to the present invention.
Figure 5:
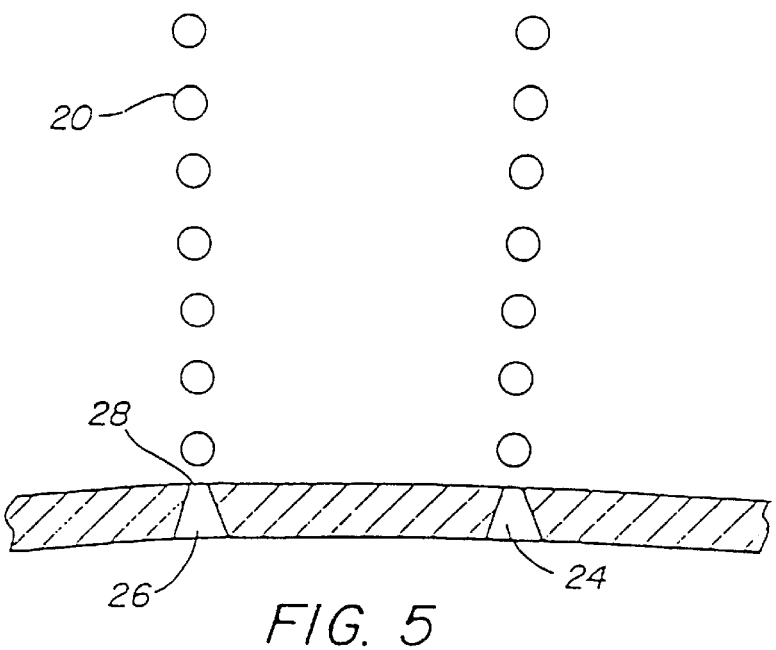
FIG. 5 is an enlarged cross-sectional view of the center area of the membrane shown in FIG. 2 and labelled "5".
Figure 6:
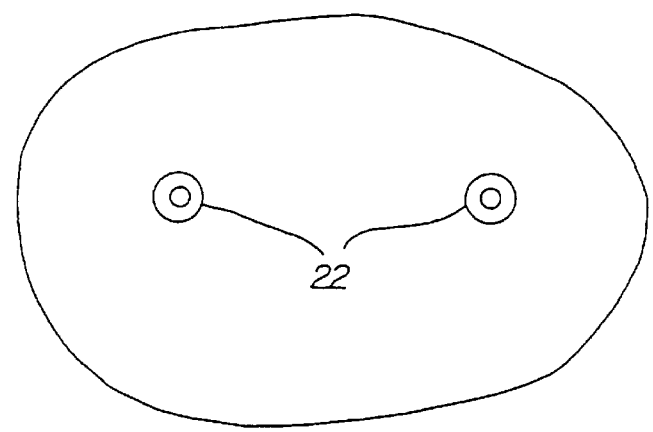
FIG. 6 is an enlarged elevational view of the center area of the vibrating surface of the present invention showing a preferred aperture shape.

The significantly larger oscillation amplitude of the center of the vibrating surface in FIG. 2, as compared to the perimeter, is due primarily to two factors. One is the shape of the vibrating surface 12 and the other is the frequency of oscillation that is selected for activation of the oscillator 18. More specifically, vibrating surface 12 is configured so that its cross-section is reduced toward the center. The vibrating surface configuration may be understood best by referring to FIGS. 2, 3, and 4, which illustrate a preferred embodiment thereof. The apertures 22 in vibrating surface 12 may be understood best by referring to FIGS. 5 and 6. As seen therein, the center portion 15 (FIG. 5) of the vibrating surface 12 is provided with apertures 22, each characterized by a tapered wall 24, forming a large opening 26 on one side of the center portion 15 and a small opening 28 on the opposite side thereof. The thickness of the center portion 15 of the vibrating surface 12 is preferably 0.003-inch. Each aperture 22 is positioned at or near the center of the vibrating surface and is circular in shape with large opening 26 having a radius of 0.006-inch and the small opening 28 thereof having a radius of 0.0025-inch.

The shape of vibrating surface 12 and, in particular, the reduction in cross-section of the vibrating surface between its perimeter 14 (FIG. 3) and its center 16, is selected to provide a significant increase in amplitude of oscillation between the perimeter and the center of vibrating surface 12. This increase in oscillation amplitude has been found to occur at particular frequencies of oscillation of the vibrating surface 12 such as at the second harmonic of the natural oscillating frequency of the vibrating surface. In the preferred embodiment of the present invention, it is desirable to have a damping ratio of at least 10 percent and to provide an amplitude ratio between the center area and the perimeter of the vibrating surface of at least 10, depending upon the voltage applied to the oscillator 18 and its mechanical responsiveness thereto.

When the center of the vibrating surface oscillates with an amplitude which exceeds a preselected threshold, fluid droplets are ejected from aperture 22 (FIG. 1) at the frequency of oscillation of oscillator 18. Thus, by controlling the amplitude of the perimeter oscillation and, thus, the amplitude of the center oscillation so that it is either above or below this threshold ejection level, the ejection of fluid droplets may be readily controlled.

In one embodiment that has been reduced to practice, the oscillation amplitude is 0.001-inch at the perimeter. The frequency of oscillation is approximately 60,000 Hz, which corresponds to the second modal frequency of the vibrating surface 12. The fluid droplet ejection level, that is, the level above which the amplitude of oscillation of the center 15 of the vibrating surface 12 causes fluid droplets to be ejected therefrom, is approximately 0.0016-inch. The perimeter oscillation is adjusted so that the center oscillation varies in amplitude from cycle to cycle, so that it is just above the ejection level and below the ejection level upon alternate cycles. The actual ejection level threshold, that is, the actual oscillation amplitude of the center of the vibrating surface which causes the ejection of fluid droplets, depends upon the characteristics of the fluid selected, as well as the shape and dimensions of the aperture 22. In the particular preferred embodiment shown herein, the ejection level is achieved using gasoline.

Figure 7:
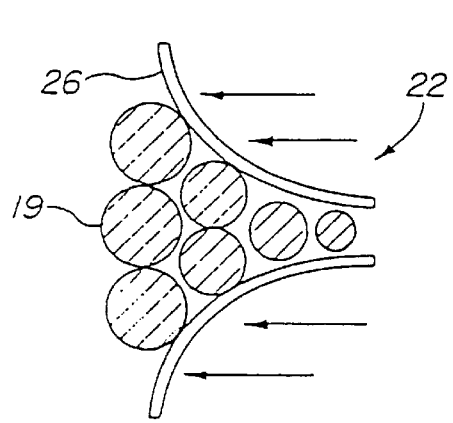
FIG. 7 is a schematic illustration of the fluid characteristic within a tapered aperture during half of an oscillation cycle.
Figure 8:
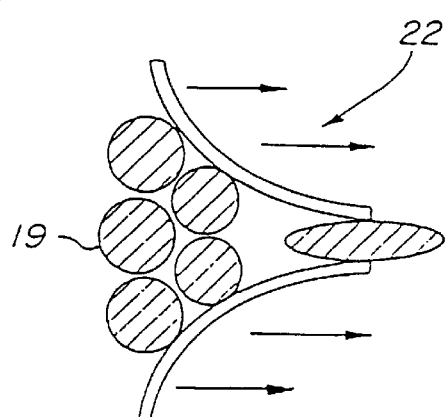
FIG. 8 is a schematic illustration of the fluid characteristic with a tapered aperture during half of an oscillation cycle.

As shown in FIGS. 7 and 8, fluid 19 continuously adheres through solid/fluid surface tension to the large opening 26 of aperture 22. The fluid is compressed in the first half of the oscillation (FIG. 7) when the vibrating surface strokes toward the fluid and decompresses in the second half of the oscillation cycle (FIG. 8) when the vibrating surface strokes away from the fluid. Droplets are ejected each time the amplitude of oscillation of the aperture element 15 (FIG. 5) exceeds the ejection level threshold. The number of droplets and spacing therebetween are a function of the frequency of oscillation. In the preferred embodiment hereof, at a 60,000-Hz oscillation frequency, it has been found that when the ejection amplitude is continually above the threshold level, droplets are attached to each other and form a continuous stream. By altering the oscillation amplitude, such as by reducing it below the threshold level every second cycle, the droplets can be separated. This feature is particularly advantageous in fuel injection systems. It will be understood, however, that with selected changes in the shape of the vibrating surface 12, the characteristic of the fluid, and in the shape and dimensions of aperture 22, the selected frequency of operation may vary from that recited herein. Nevertheless, based upon the preferred embodiment disclosed herein, it will now be understood that ejection may be achieved by the present invention and that, in fact, fluid-droplet ejection at frequencies exceeding 60,000 Hz is readily achieved.

Figure 9:
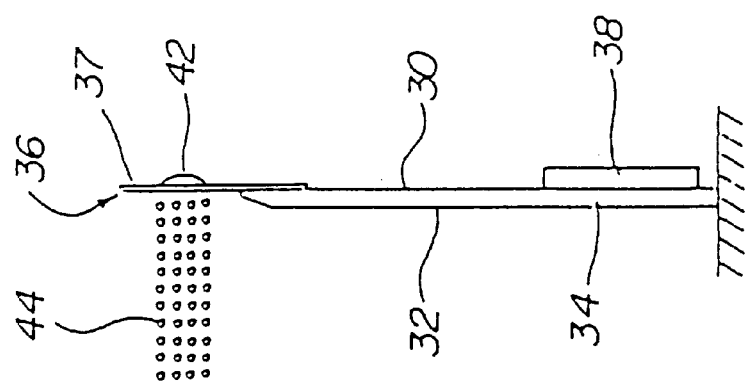
FIG. 9 is a side view of an alternate preferred embodiment of the fluid ejection device according to the present invention.

FIG. 9 illustrates an alternate preferred embodiment of the fluid ejection device 30 of the present invention which comprises a cantilever beam 32 including a base portion 34 and a free end 36. The base portion 34 is affixed to a piezoelectric oscillator 38. The free end 36 of the beam 32 is provided with a planar surface through which there are nine microscopic tapered apertures. Fluid 42 is in contact with the free end 36 through which droplets 44 are ejected.

Figure 11:
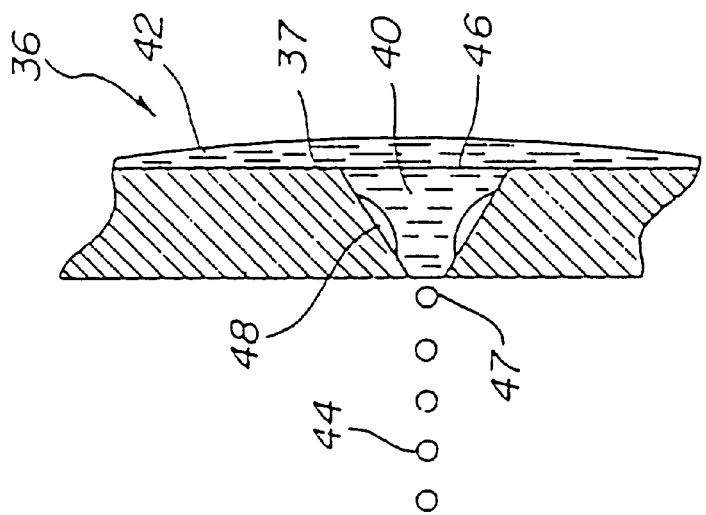
FIG. 11 is an enlarged cross-sectional side view of the free end of the fluid ejection device of FIG. 9.
Figure 10:
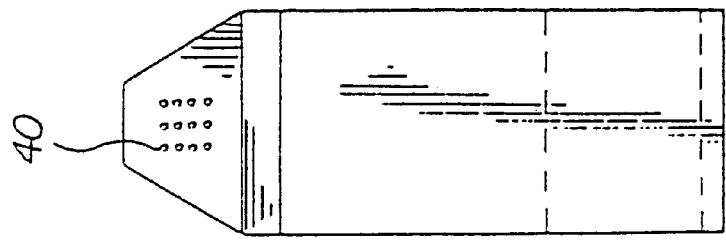
FIG. 10 is a front view of the fluid ejection device of FIG. 9.

FIG. 10 provides a front view of the fluid ejection device 30 and best illustrates the apertures 40. FIG. 11 is an enlarged cross-sectional side view of the fluid ejection device 30 showing the free end 36 in contact with the fluid 42. The large opening 46 of each aperture 40 is in surface tension contact with the fluid 42. The piezoelectric element 38 (FIG. 9) produces high-frequency oscillations at the base end 34 of the beam 32. The planar surface 37 at the free end 36 oscillates at the same frequency as the base 34, but with much greater amplitude. Such oscillation of the free end 36 is due primarily to two factors: the beam 32 is shaped such that its moment of inertia is reduced toward the free end 36; and the induced frequency is substantially the natural frequency of the beam 32.

The oscillation of the planar surface 37 produces cycles of pressure fluctuation at the interface between the fluid 42 and the surface 37 and inside the apertures 40 and, particularly, near the inside wall 48 of each aperture, is significantly more intense as compared to the pressure fluctuation near the planar surface 37. This characteristic is exclusively attributed to the conical cross-sectional geometry of the apertures 40. As a result, fluid cavitation is developed inside each aperture 40 at an oscillation amplitude that is too small to dynamically disturb the fluid 42 near the planar surface 37. The cavitation inside the aperture 40 produces a negative pressure that draws fluid from the planar surface 37 into the large opening 46 of the aperture 40 and ejects a stream of droplets 44 from its small opening 47 to a great distance. The ultrasonic oscillations do not break up or nebulize the fluid 42 at the surface 37, such fluid remaining dynamically at rest during the ejection of fluid 42 within the aperture 40. Ejection continues until all the fluid 42 is drawn from the surface 37 and ejected forwardly as droplets 44. In this preferred embodiment, the diameter of the large opening 46 of the aperture 40 is 0.006" and the diameter of the small opening 47 is 0.0025". The thickness of the planar surface 37 is 0.003" and the oscillation frequency is 50 kHz, which is the third natural frequency of the beam 32.

Figure 12:
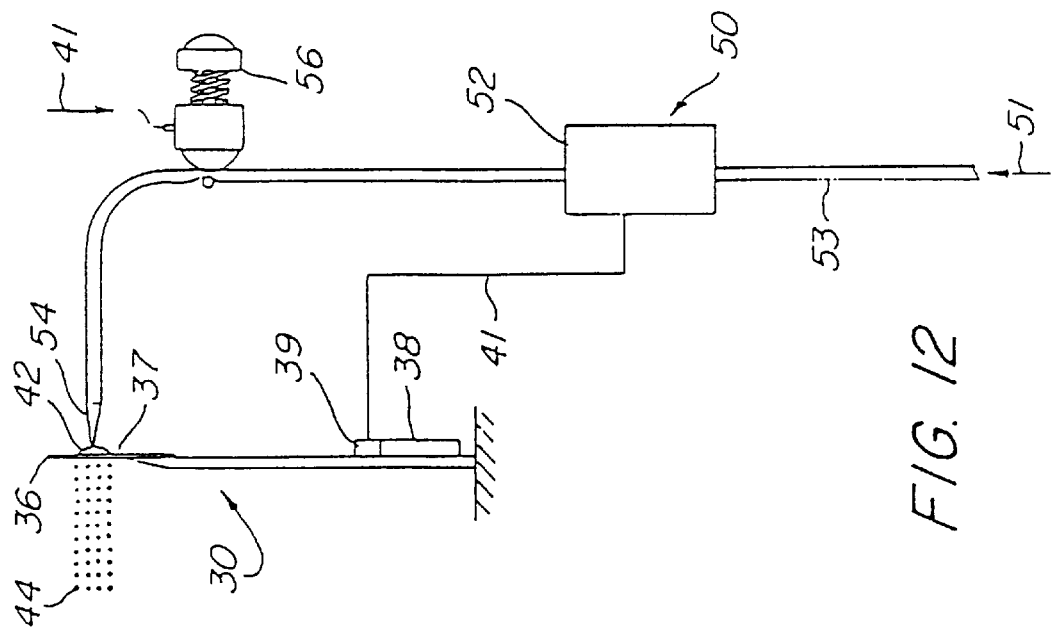
FIG. 12 illustrates the ejector of FIG. 9 provided with a fluid supply system.

Referring now to FIG. 12, the ejector 30 described in the specification with respect to FIGS. 9, 10, and 11 is now provided with a fluid supply system 50 that continuously transports fluid 51 to wet the oscillating surface 37 via a supply tube 53 ending at a supply nozzle 54. The fluid 51 is transported to the surface 37 at a rate which is lower than the maximum ejection rate of the apertures 40 to prevent overflow of fluid 42 from the supply side of the oscillating surface 37. A pinch valve 56 controls delivery of the fluid 51 to the oscillating surface 37. The fluid supply system 50 is connected to an electronic flow control valve 52 which, in the preferred embodiment, is made by ICS sensors. The valve 52 is connected to an electronic circuit that detects the amount of liquid 42 on the oscillating surface 37. In the event of excessive delivery of fluid, the oscillation amplitude decreases and the current draw by the piezoelectric element 38 decreases. A current sensor circuit 39 senses the current draw and transmits an overflow signal 41 to the flow control valve 52 to reduce the delivery rate of liquid 51 to the surface 37 until the amount of fluid returns to a normal level.

Figure 13:
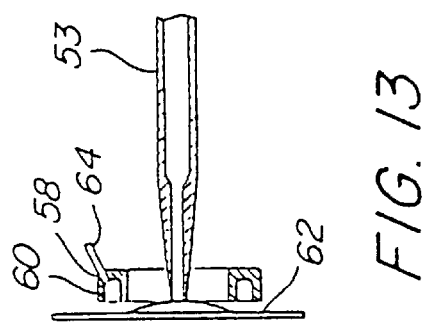
FIG. 13 illustrates an alternative apparatus for preventing accidental overflow in the fluid supply system of FIG. 12.

FIG. 13 illustrates an alternative apparatus for preventing fluid overflow with the fluid supply system 50. An additional ring element 58 including a slot 60 is installed near the oscillating surface 37 such that the slot 60 is positioned a predetermined distance from the boundary 62 of the fluid 42. The preferred ring element 58 is manufactured by Clippard Instruments Laboratory, Inc. of Cincinnati, Ohio and is designated as Model No. 1022. The slot 60 is connected to a suction venturi pump (not shown) through an inlet 64. A suction venturi pump, designated as Part No. 16480, is commercially available from Spraying Systems Co. of Wheaton, Ill. In the event of overflow, the boundary 62 of the fluid 42 expands toward the ring 58 and returns to the supply line 53.

FIG. 13A illustrates a further alternative apparatus 200 for preventing fluid overflow when dispensing liquid through vibrating tapered apertures in the manner previously described. The apparatus 200 operates under similar principles as those described in connection with the apparatus of FIG. 13. The apparatus 200 is particularly useful in applications requiring high flow rates, e.g. gallons per hour, such as with the injection of gasoline into an engine.

The apparatus 200 includes a housing 202, a delivery fluid path 204, and a return fluid path 206. An inlet port 208 is in communication with the delivery fluid path 204 and an exit port 210 is in communication with the return fluid path 206. Connected to the housing 202 by a bolt 212 or other securing member is a vibratable member 214. Vibration is provided to the member 214 by an ultrasonic transducer 216. Tapered apertures (not shown) are provided in the vibratable member 214 for ejecting liquid from the member 214 when vibrated by the transducer 216 in the manner previously described. The housing 202 further includes a liquid outlet 204b for supplying liquid to the vibrating member 214. A venturi suction arrangement 220 that is connected to the return fluid path 206 and to the delivery fluid path 204.

Operation of the apparatus 200 is as follows. Fluid is supplied to the apparatus 200 through the inlet port 208. About two-thirds of the liquid flows through the path 204 and from the outlet 204b to the vibratable member 214. About one-third of the liquid flows through the venturi suction arrangement 220 causing intense suction at the fluid path 206. The fluid path 206 is in communication with the a flow path 218 so that the suction action can be transferred to an inlet opening 218a of path 218. The suction developed near the opening 218a collects any excess liquid that has not been ejected and prevents overflow. The liquid that is supplied to the venturi arrangement 220 and the liquid that returns from the path 218 exit the apparatus 200 from port 210 where it can be discharged or recirculated.

In a preferred embodiment, the apparatus 200 was installed in an air intake manifold of a small gasoline engine, model CV-14, from Kohler Engine, Kohler, Wis. The gasoline supply was disconnected from the engine carburetor and was instead connected to the supply port 208 of apparatus 200. Apparatus 200 provides superior control over the supply of atomized gasoline to the engine in comparison to a conventional carburetor. Preferably, the amount of gasoline and the time of ejection is controlled by a conventional engine management system, such as model LS-14 from Fuel Management Systems, Mendelein, Ill. It has been found that apparatus 200 is particularly advantageous for use in small two cycle internal combustion gasoline engines for reducing exhaust emission.

FIG. 14 shows the ejection device 30 of FIG. 9, further including an alternative fluid supply system 70 and an electrical wave generator 71 including a battery or external power inlet (not shown) to activate the piezoceramic element. The ejector device 30 is preferably attached to a platform 72 of the supply system 70 at the piezoelectric oscillator 38. The supply system 70 includes a fluid supply container 74 which is preferably made from a flexible, disposable nylon material. A discharge nozzle 76 is affixed at a side wall of the supply container 74 providing fluid communication between fluid in the tube and the ejection device 30. When force is applied to the side of the supply container 74, the fluid inside the supply container 74 is pressurized an forced through the discharge nozzle 76.

The supply system 70 further includes a discharge valve apparatus 80 which is preferably attached to the platform 72. The preferred discharge apparatus 80 includes a spring-loaded plunger 82 acting on the external side wall of the supply container 74 against a rear opening of the discharge nozzle 76 to prevent unwanted discharge of fluid from the supply container 74. When the plunger 82 is released, fluid is discharged toward the oscillating surface 37. Fluid enters into a gap 84 between the nozzle 76 and the surface 37 and is held by surface tension contact. In the preferred embodiment this gap is 0.025".

Figure 14:
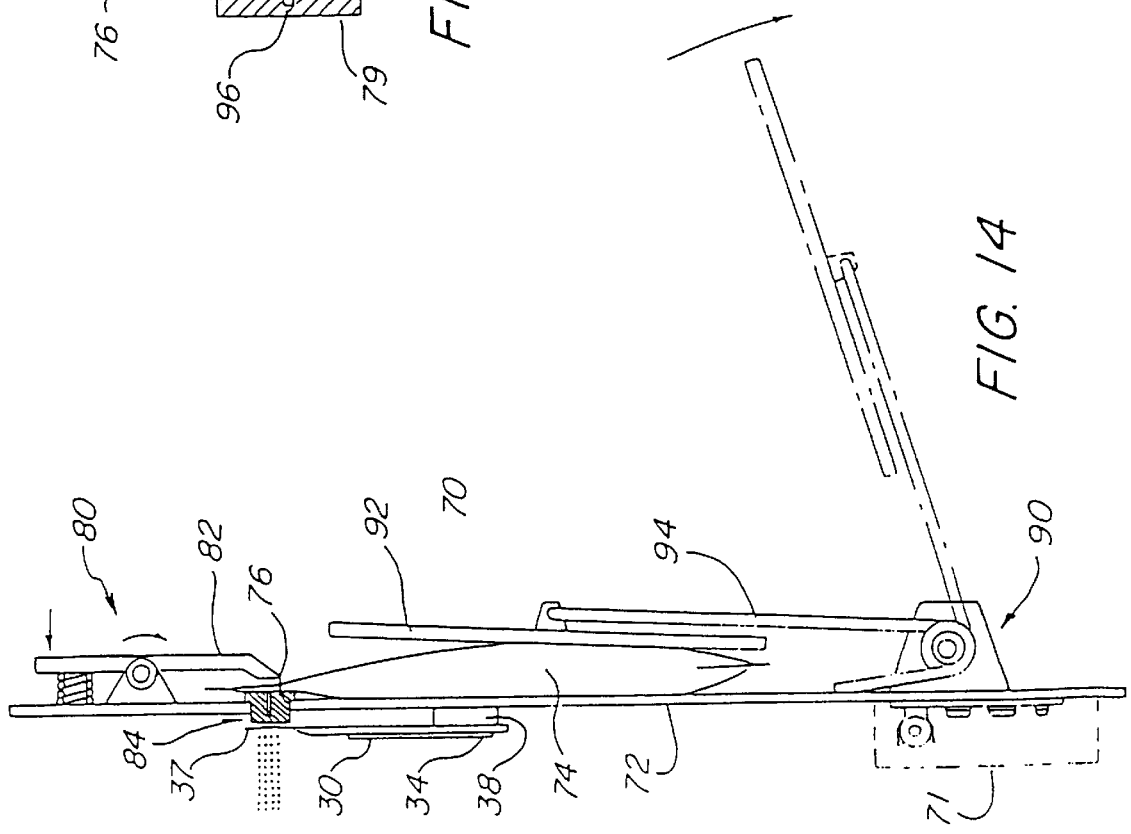
FIG. 14 illustrates the ejector of FIG. 9 provided with an alternative fluid supply system.

The alternative fluid supply system 70 additionally provides a means for applying mechanical pressure 90 on the nylon container 74 to force the fluid through the nozzle 76. The pressure-applying means 90 includes a pressure plate 92 pivotally attached to a torsion spring 94 for applying a compressive force on a side wall 75 of the container 74. As shown in FIG. 14, the pressure plate 58 can be rotated clockwise to a released position, facilitating the unloading and loading of fluid supply containers 74. In operation, the pressure plate 92 applies a continuous pressure of approximately 10 psi to the fluid inside the nylon container 74.

Figure 15:
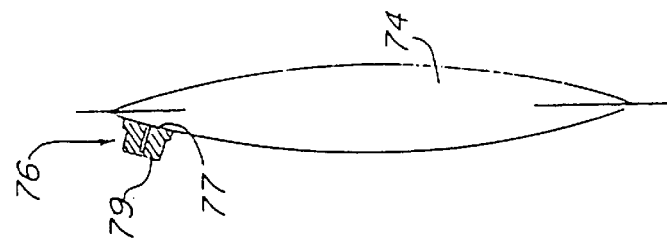
FIG. 15 is an enlarged cross-sectional side view of the fluid supply tube of FIG. 14 including a discharge nozzle attached at a side wall of the supply tube.

FIG. 15 provides an enlarged cross-sectional side view of the supply container 74 including an integrally-formed discharge nozzle 76 attached at a side wall of the container 74. The nozzle includes a rear surface 77 in fluid communication with fluid inside the supply container 74 and a front surface 79 positioned in close proximity to the vibrating free surface 37.

Figure 16:
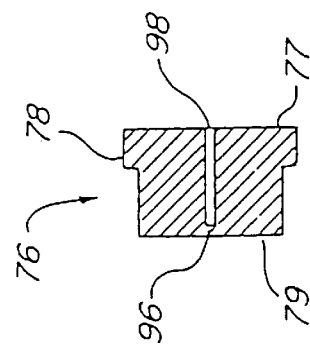
FIG. 16 is an enlarged cross-sectional side view of the discharge nozzle of FIG. 14.

FIG. 16 provides an enlarged cross-sectional side view of the discharge nozzle 76. As can be readily appreciated, a circumferential ridge 78 formed around the discharge nozzle 76 ensures that the gap 84 is maintained at its preferred distance. The nozzle 76 is preferably made of an elastomer material and includes a cut 96 through part of its thickness. The cut 96 is normally closed because of the natural elasticity of the elastomer material. Fluid pressure applied to the rear side of the nozzle opening 98 forces the cut 96 to open and allow passage of liquid to the oscillating surface 37. The discharge nozzle 76 is designed to keep the fluid in the supply tube 76 hermetically sealed when the fluid ejection device 30 is not in use.

FIG. 17 illustrates another alternative preferred embodiment of the fluid ejection device wherein the oscillating surface comprises a curved member 100 with two piezoelectric elements 102a, 102b respectively affixed to front surfaces 104a, 104b. The piezoelectric elements 102a, 102b impart oscillations to a thin angled surface 106 located centrally on the curved member 100, causing fluid 108 to be ejected forwardly as a divergent stream of droplets 110. A predetermined curvature characteristic of the angled surface 106 results in a wider distribution of the droplets 110 within an ejection angle 112. FIG. 18 provides a front view of the curved member 100 and further illustrates that the angled surface 106 is bound on its perimeter by a window opening 114. Preferably, the angled surface 106 includes 45 apertures 116 in a 5×9 matrix.

FIG. 19 is a schematic view of a fluid delivery system 224 for regulating the flow of liquid 226 to an oscillating surface 228 having a plurality of tapered holes (not shown) for dispensing liquid as previously described. The fluid delivery system 224 is configured so that the volumes of liquid delivered to the oscillating surface 228 are substantially equal to the volumes of liquid ejected from the oscillating surface 228. The fluid delivery system 224 is further configured so that the liquid 226 is delivered to the oscillating surface 228 at a rate that is substantially equal to the rate of ejection from the surface 228.

The fluid delivery system 224 includes a central reservoir 230 for storing the liquid 226 and a fluid channel 232 extending from the central reservoir 230. The fluid channel 232 has a distal end 234 that is spaced apart from the oscillating surface 228. The fluid delivery system 224 further includes a gas or an air vent 236 having an open distal end 238 that is near the distal end 234 of the fluid channel 232 and is spaced apart from the oscillating surface 228. With such a configuration, the liquid 226 flows by force of gravity from the central reservoir 230, through the fluid channel 232, and out the distal end 234. As the liquid 226 is delivered to the oscillating surface 228, a liquid bead 240 is formed. The liquid 226 flows from the central reservoir 230 until the bead 240 becomes large enough to occlude the distal end 238 of the air vent 236. As the distal end 238 of the air vent 236 is filled with liquid from the bead 240, air is prevented from flowing to the central reservoir 230 from the air vent 236, thereby creating a vacuum in the central reservoir 230 and preventing further fluid flow through the fluid channel 232. As liquid from the bead 240 is ejected from the oscillating surface 228 in the manner previously described, the bead 240 is reduced in size allowing air to enter into the vent 236 and allowing additional fluid to flow through the fluid channel 232. In this manner, a continuous supply of liquid 226 is provided to the oscillating surface 228 in amounts that are substantially equal in volume to the amount of liquid dispensed from the oscillating surface 228 and at a rate that is equal to the rate of ejection.

An alternative embodiment of a fluid delivery system 242 is schematically illustrated in FIG. 20. The fluid delivery system 242 includes a central reservoir 244 and a fluid channel 246 that are both filled with a liquid 248. The fluid delivery system 242 operates under the same principles as the fluid delivery system 224, i.e. by controlling air flow to the reservoir 244. Specifically, liquid 248 flows through a distal end 250 of the fluid channel 246 by capillary forces to form a liquid bead 252 on an oscillating surface 254. An air vent 256 is provided in the fluid channel 246 for supplying air to the central reservoir 244. As the liquid 248 travels through the fluid channel 246 to reach the oscillating surface 254, some of the liquid 226 flows into the air vent 256 to close the air vent 256. At this point, air is prevented from flowing into the central reservoir 244 via the air vent 256, thereby creating a vacuum in the reservoir 244 and stopping the flow of liquid 248 from the central reservoir 244. As liquid from the bead 252 is ejected from the oscillating surface 254, fluid is drained from the air vent 256 and flows toward the distal end 250 to replace the liquid ejected. As the fluid is drained from the air vent 256, the air vent 256 is opened to allow air to flow through the fluid channel 246 and into the central reservoir 244. An amount of liquid 248 equal in volume to the volume of air supplied to the central reservoir 244 via the air vent 256 then flows through the channel 246 to again fill the air vent 252 and to resupply liquid ejected from the bead 252. By tailoring the dimensions of the fluid delivery system 242, the volume of air entering the reservoir 244 can be easily controlled so that a continuous supply of liquid 248 is supplied to the oscillating surface 254 in an amount equal in volume the amount of the liquid dispensed from the oscillating surface 254 and at a rate equal to the rate of ejection.

Figure 21:
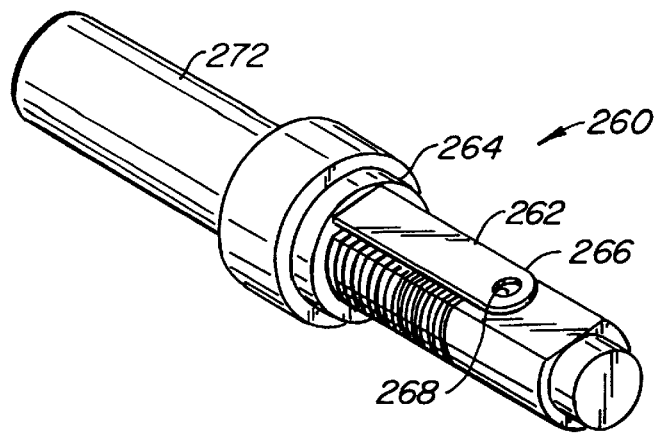
FIG. 21 is a perspective view of an exemplary dispensing apparatus having a flow regulator for regulating the flow of liquid to a vibratable member that is used to dispense the liquid.

Referring to FIG. 21, an exemplary embodiment of an apparatus 260 for dispensing liquid as an atomized spray is shown in perspective view. The apparatus 260 is patterned after the delivery system 242 of FIG. 20 and is particularly useful for relatively small flow rates, i.e. milliliters per hour. The apparatus 260 includes a vibratable member 262 that is connected to a housing 264. Within the housing 264 is an ultrasonic transducer element (not shown) for vibrating the member 262 at an ultrasonic frequency. At a distal end 266 of the member 262 is an aperture plate 268 having a plurality of apertures (not shown) for dispensing liquid when the member 262 is vibrated. The apertures in the plate 268 are tapered with the apertures having a larger cross-sectional area at a rear surface 269 (see FIG. 22B) of the vibratable member 262. The rear surface 269 in turn faces a holding surface 270 on the apparatus 260. The aperture plate 268 is preferably in contact with the holding surface 270, but can be spaced apart from the holding surface, usually by distances up to about 1.0 mm and sometimes greater.

As described in greater detail hereinafter, liquid on the holding surface 270 is supplied from a supply container 272. As liquid is delivered to the holding surface 270, a thin layer of liquid is developed on the holding surface 270. The liquid film is placed in contact with the aperture plate 268 so that upon vibration of the member 262 liquid is ejected from the apertures in the plate 268 in the manner described with previous embodiments. The liquid is held to the rear surface 269 of the plate 268 by surface tension forces. Preferably, the surface tension forces will be the exclusive forces holding the liquid to the plate 268 until the liquid is ejected. In this way, liquid will not overflow and spill from the holding surface 270 during operation. The supply container 272 is preferably removably attached to the housing 264 so that new or different supplies of liquid can easily be provided by removing and refilling the supply container 272 or by providing a new container 272.

Figure 22B:
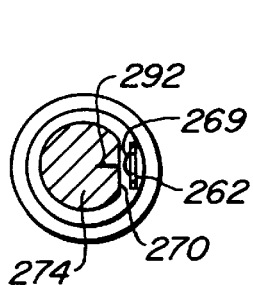
FIG. 22B is a cross-sectional view of FIG. 22 taken along lines B—B.
Figure 22:
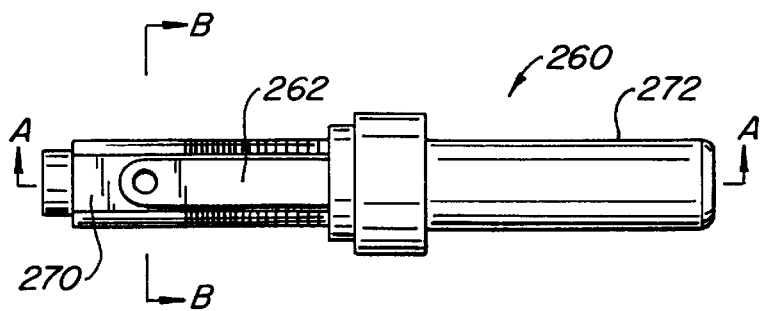
FIG. 22 is a top view of the dispensing apparatus of FIG. 21.
Figure 23:
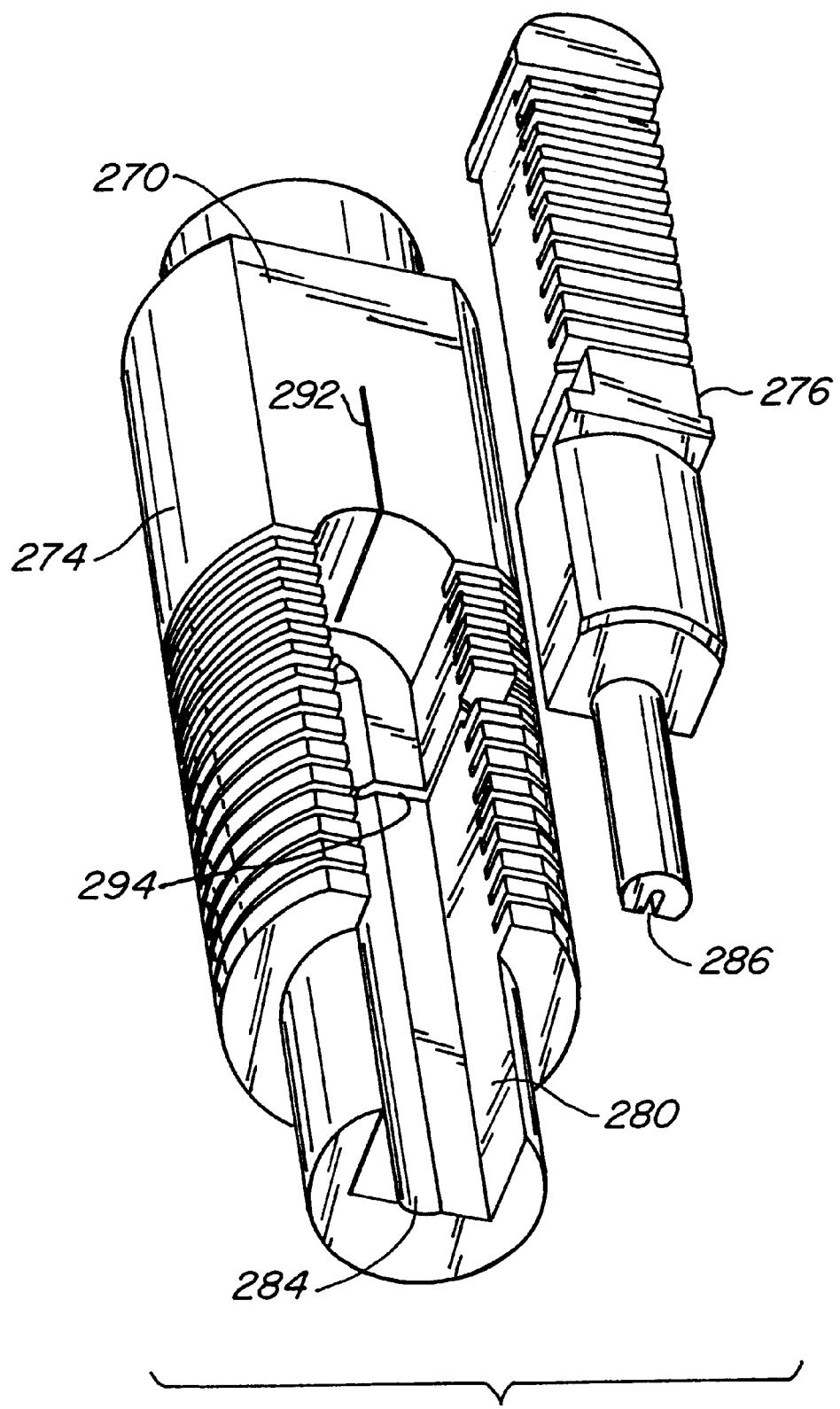
FIG. 23 is an exploded view of a distal portion of the apparatus of FIG. 21.

Referring to FIGS. 22–23, delivery of liquid from the container 272 to the holding surface 270 will be described. The housing 264 includes a longitudinal member 274, an insert 276, and a holding member 278. The holding member 278 holds the vibratable member 262 over the holding surface 270 and includes the ultrasonic transducer for vibrating the member 262. As best shown in FIG. 23, the insert 276 is inserted into an elongate groove 280 in the longitudinal member 274 to form a fluid path 282 extending between the longitudinal member 274 and the insert 276. The insert 276 is removably held within the longitudinal member 274. Configuring the connection between the longitudinal member 274 and the insert 276 in this manner is advantageous for ease of manufacture. The longitudinal member 274 and the insert 276 can be made from parts modified from a fountain pen, commercially available from Sheaffer Inc., Ft. Madison, Iowa.

The fluid path 282 is formed b a groove 284 in the longitudinal member 274 and a channel 286 in the insert 276. A proximal end 288 of the fluid path 282 is in communication with the supply container 272, while a distal end 290 of the fluid path 282 is in communication with a slit 292 in the longitudinal member 274. In turn, the slit 292 is in communication with the holding surface 270. In this manner, liquid from the supply container 272 is delivered to the holding surface 270 via the fluid path 282 and the slit 292.

Figure 22A:
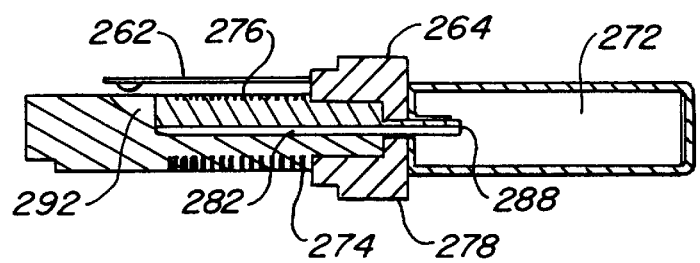
FIG. 22A is a cutaway view of FIG. 22 taken along lines A—A.

Referring to FIGS. 22A and 22B, configuration of the slit 292 will be described in greater detail. The slit 292 preferably has a width that is narrow enough to allow for liquid to be drawn through the slit 292 by capillary forces. Preferably the width of the slit 292 is in the range from about 0.002 inch to 0.005 inch, and more preferably at about 0.004 inch. In this way, liquid reaching the distal end 290 of the fluid path 282 is drawn through the slit 292 and to the holding surface 270 by capillary action.

Figure 24A:
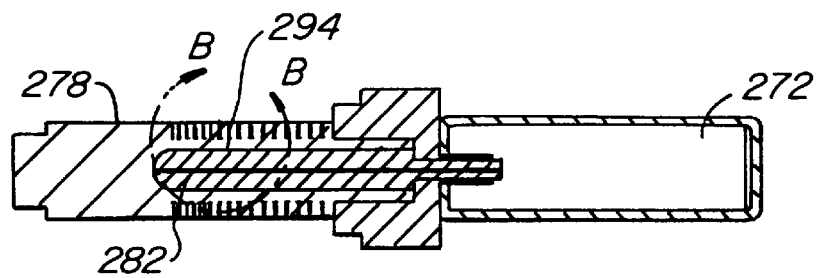
FIG. 24A is a cutaway view of the dispensing apparatus of FIG. 24 taken along lines A—A.
Figure 24:
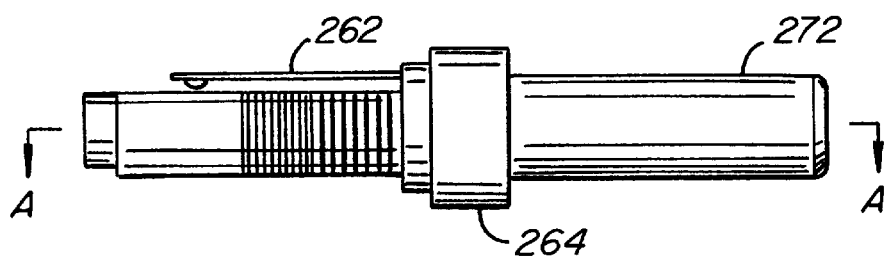
FIG. 24 is a side view of the dispensing apparatus of FIG. 21.
Figure 24B:
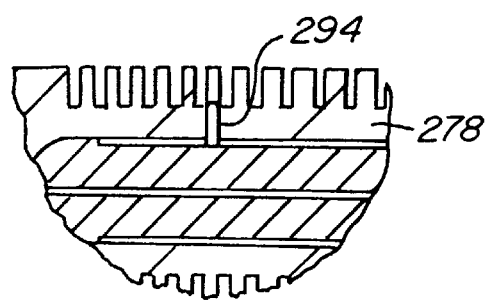
FIG. 24B is an enlarged view of the region B—B of the dispensing unit of FIG. 24A.

Referring to FIGS. 23, 24A, and 24B, regulation of the flow of liquid from the supply container 272 and to the holding surface 270 will be described. In communication with the fluid path 282 is a gas or air vent 294. The air vent 294 is formed in the longitudinal member 278 and allows air from the atmosphere to flow into the supply container 272 via the fluid path 282. The supply container 272 is sealed about the housing 264 so that the interior of the supply container 272 can only communicate with the outside atmosphere via the fluid path 282. As liquid is transferred from the supply container 272, a vacuum is created within the container 272, thereby preventing further flow of liquid from the container 272 until the container 272 is vented. In this way, the flow of liquid from the container 272 and to the holding surface 270 is regulated by controlling the amount of air supplied to the container 272.

The amount of liquid supplied to the holding surface 270 will preferably be sufficient to cover at least a portion of holes of the aperture plate 268 without overflowing from the holding surface 270 and creating a messy and wasteful working environment. Upon vibration of the aperture plate 268, some of the liquid is ejected from the holding surface 270. The ejected liquid is replaced with an equal amount of liquid, preferably at a rate that is equal to the rate of ejection. As described below, delivery of liquid in this manner is accomplished by supplying air to the container 272 in volumes that are sufficient to replace the volumes of liquid delivered to the holding surface 270 and at a rate that is equal to the rate of ejection.

Upon connection of the supply container 272 to the housing 264, fluid flows from the container 272 and into the fluid path 282. Preferably, the apparatus 260 will be elevated to have the container 272 above the holding surface 270 to allow gravity to assist in transferring liquid through the fluid path 282. The liquid flows through the fluid path 282 until reaching the air vent 294. At this point, some of the liquid begins filling the air vent 294 while the remainder continues through the fluid path 282 and to the slit 292. The liquid that reaches the slit 292 is drawn by capillary action through the slit 292 and to the holding surface 270. At the same time, the air vent 294 continues to fill with liquid until sufficient liquid is within the air vent 294 to close the vent 294 and prevent air from the atmosphere from entering into the supply container 272. With no air entering the supply container 272, a vacuum is created within the container 272, thereby preventing further flow of liquid from the container 272.

The size, length, and relative orientation of the supply container 272, the fluid path 282, the slit 292, and the air vent 294 can be varied to tailor the amount of liquid reaching the holding surface 270. The particular configuration of these elements can be experimentally obtained based on the properties of the liquid involved. In one preferable aspect, the air vent 294 has a width in the range from 0.002 inch to 0.003 inch, a length in the range of about 0.005 inch to 0.010 inch, and is distanced from the supply container 272 by a length of about 0.5 inch when used with a supply container 272 having a volume of about 2 cm$^3$.

Upon vibration of the vibratable member 262, the liquid initially supplied to the holding surface 270 is ejected from the aperture plate 268. As liquid is ejected from the holding surface 270, additional liquid is drawn through the slit 292 by capillary action to replace the dispensed liquid. As liquid is drawn through the slit 292, liquid in the air vent 294 drains into the fluid path 282 to replace the liquid. When liquid drains from the air vent 294, the air vent 294 reaches an open configuration to allow air to enter into the vent 294 where it travels to the supply container 272 via the fluid path 282. Delivery of air to the container 272 in this manner reduces the amount of vacuum existing in the container 272 and allows an amount of liquid to be transferred into the fluid path 282 until the threshold vacuum pressure is again reached in the container 272. As fluid is transferred into the fluid path 282, the air vent 294 again closes as previously described. Hence, by tailoring the configuration of the dispensing apparatus 260, a continuous supply of liquid can delivered to the holding surface 270 for ejection by the aperture plate 268 in an amount that is substantially equal to the amount dispensed and at a rate that is equal to the ejection rate. This ensures that sufficient (but not excessive) fluid will be supplied to the aperture plate 268 for ejection.

The housing 264 will preferably be constructed of a plastic material having good surface wetting capabilities, such as ABC plastic, and particularly, Cycloac. To assist the flow of liquid through the fluid path 282 and the slit 292, a small amount of liquid surfactant can be added to the liquid. The apparatus 260 can be employed to dispense a variety of liquids such as water, ink, alcohol, gasoline, deodorants, insecticides,medicaments, and other liquids having applications where atomization of the liquid is needed.

One particular advantage of the apparatus 260 is that the flow of liquid from the supply container 272 to the aperture plate 268 is controlled without the use of the moving elements, electrical circuits, mechanical valves, or the like. Instead, the flow of liquid is controlled by the liquid itself as the liquid fills and is drained from the air vent 294. Such an apparatus is easy to manufacture, use and to refill with new liquid, thereby reducing purchase and maintenance costs and providing convenience.

Figure 25:
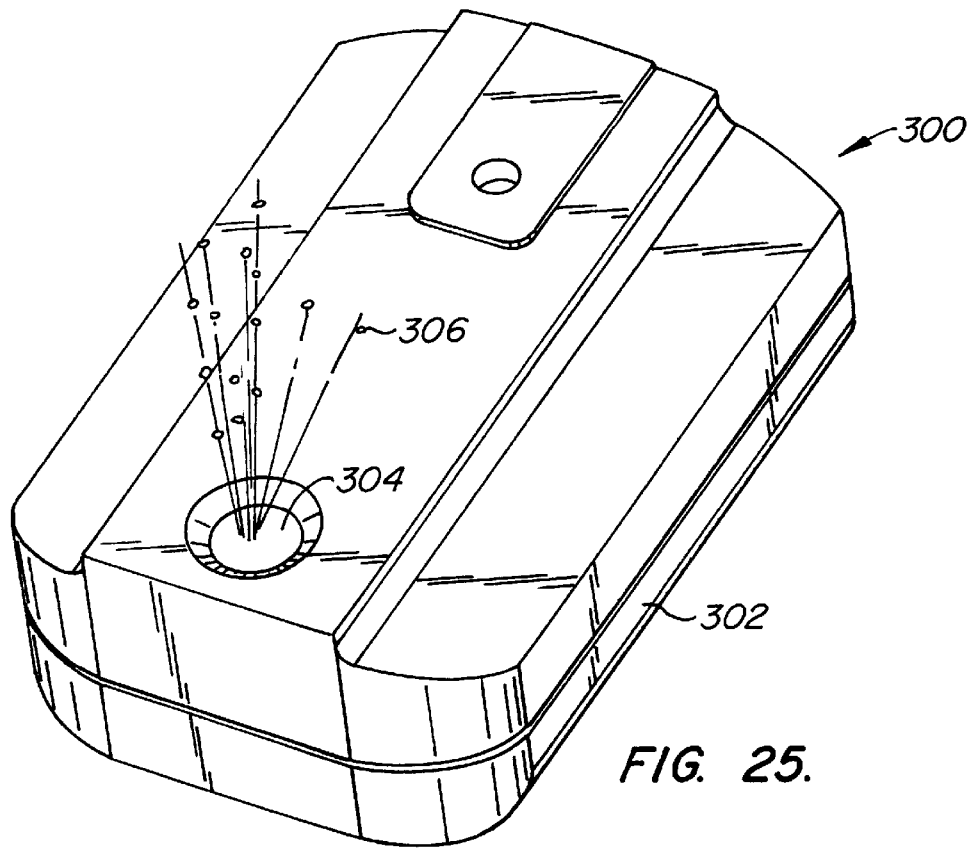
FIG. 25 is a perspective view of an exemplary dispensing apparatus having a housing enclosing a vibratable member.
Figure 26:
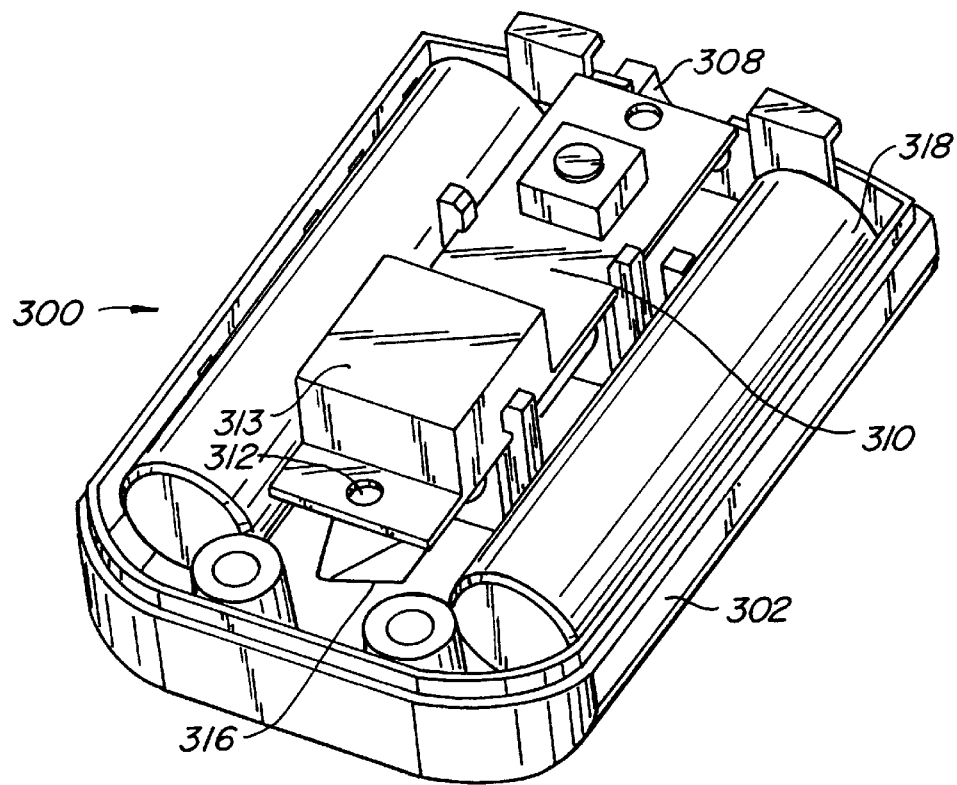
FIG. 26 illustrates the dispensing apparatus of FIG. 25 with a top portion of the housing removed.

Referring to FIGS. 25 and 26, an alternative embodiment of an exemplary dispensing apparatus 300 will be described. The apparatus 300 includes a housing 302 that is separable into two halves. The housing 302 is provided with at least one ejection port 304 for ejecting liquid 306. The housing 302 further includes an application port 308 for attaching a supply of liquid.

Within the housing 302 is a vibratable member 310 having an aperture plate 312 mounted therein. The aperture plate 312 is aligned with the ejection port 304 so that liquid ejected from the aperture plate 312 is dispensed through the ejection port 304 as illustrated in FIG. 25. The aperture plate 312 includes a plurality of tapered apertures similar to the aperture plates previously described. Circuitry 313, including a transducer, is provided for vibrating the vibratable member 310 so that liquid can be dispensed through the apertures in the aperture plate 312 as previously described.

To supply liquid to the aperture plate 312, a liquid delivery system 316 is provided. The liquid delivery system 316 is preferably vertically angled in the housing 302 so that gravity can assist in the flow of liquid toward the aperture plate 312. The liquid delivery system 316 can be essentially identical to the dispensing apparatus 260 described in FIG. 21. The circuitry 313 further includes an electronic timer for cyclically actuating the transducer 314. To provide power to the transducer 314, the apparatus 300 further includes a pair of batteries 318, such as commercially available AAA-type batteries.

By configuring the dispensing apparatus 300 as just described, a number of advantages are provided. Use of the batteries 318 as a power source allows the dispensing apparatus 300 to be placed in a wide variety of locations (particularly remote locations where conventional power outlets are not available). For example, in one preferable aspect, the dispensing apparatus 300 is useful as an insecticizer. Use of the batteries 318 allows the apparatus 300 to be placed in remote locations, such as in an attic, near a patio, in a garage, or the like.

A further advantage of the dispensing apparatus 300 is that it can be preprogrammed with a dispensing cycle, e.g. ejecting liquid five seconds each five minutes. In this way, the ejection of liquid can be programmed to precisely control the amounts of liquid that are dispensed into the atmosphere. Programming the apparatus 300 in this way is desirable in many applications where safety is a concern and precise control of the amount of liquid dispensed is critical. As one example, the dispensing apparatus 300 is useful in controlling the dispensing of an insecticide such as a pyrethroid insecticide sold under the name Sumithrin. By programming the apparatus 300 with a dispensing cycle, safety is provided by ensuring that too much insecticide will not be dispensed, particularly when used near inhabited locations. At the same time, programming allows a sufficient amount of liquid to be ejected so that the apparatus 300 is effective as an insecticizer. Reliability is also provided since regulation of the flow of liquid to the aperture plate 312 is provided by an air vent and involves no moving or electrical parts.

As one example, which is not meant to be limiting, when used as an insecticizer, the apparatus 300 preferably dispenses the insecticide at a rate in the range from 0.5 $cm^3$ to 2 $cm^3$ per hour, with droplet sizes being in the range from 3 micron to 10 micron. Usually, the vibratable member is vibrated at a frequency in the range from 20 kHz to 200 kHz. When used as an air freshener, the apparatus 300 preferably dispenses the air freshener at a rate in the range from 1 $cm^3$ to 2 $cm^3$ per hour, with droplet sizes being in the range from 3 micron to 10 micron.

In still a further advantage, the dispensing apparatus 300 is relatively inexpensive to manufacture and operate thereby providing a convenient alternative to a consumer in his choice of dispensing apparatus. For example, operating costs usually only include the cost of batteries and the liquid. In one alternative, the batteries can conveniently be included as part of the supply container so that each time a new container is connected to the port 308, the batteries are replaced. This allows the batteries and the liquid supply container to be sold together as a single disposable unit.

It will now be understood that what has been disclosed herein comprises a novel and highly innovative fluid ejection device readily adapted for use in a variety of applications requiring the ejection of small droplets of fluid in a precisely controlled manner.

Those having skill in the art to which the present invention pertains will now, as a result of the Applicant's teaching herein, perceive various modifications and additions which may be made to the invention. By way of example, the shapes, dimensions, and materials disclosed herein are merely illustrative of a preferred embodiment which has been reduced to practice. However, it will be understood that such shapes, dimensions, and materials are not to be considered limiting of the invention which may be readily provided in other shapes, dimensions, and materials.

What is claimed is:

1. A method for dispensing liquid droplets as an atomized spray, the droplets being ejected from a vibratable member having a front surface and a rear surface, the member having at least one tapered hole between the surfaces for dispensing the liquid, wherein the tapered hole has a larger cross sectional area at the rear surface than at the front surface, and wherein the liquid is held in surface tension contact with the large opening of the hole, the liquid being delivered from a supply container, the method comprising:

delivering a discrete volume of liquid from the supply container to the rear surface of the vibratable member sufficient to cover the hole with liquid, wherein the discrete volume of liquid is held to the rear surface of the vibratable member by surface tension contact;

vibrating the vibratable member to dispense at least a portion of the liquid through the hole and from the front surface; and delivering additional volumes of liquid from the supply container and to the rear surface, with the additional volumes being held in surface tension contact to the rear surface of the vibratable member.

2. The method of claim 1, wherein the additional liquid is delivered to the rear surface of the vibratable member at a rate that is substantially equal to the rate of the liquid being dispensed from the front surface.

3. The method of claim 1, further comprising exchanging preselected volumes of gas with liquid from the supply container to deliver the additional volumes of liquid to the rear surface.

4. The method of claim 3, wherein the preselected volumes of gas are sufficient to replace the volumes of liquid that are delivered from the supply container and to the rear surface.

5. The method of claim 4, further comprising controlling supply of the gas volumes to the supply container by closing and opening a gas vent that is in communication with the supply container.

6. The method of claim 5, wherein the gas vent is closed upon filling of the gas vent with liquid delivered from the supply container upon delivery of the liquid to the rear surface of the vibratable member.

7. The method of claim 6, wherein the gas vent is opened upon transfer of liquid from the gas vent and to the rear surface as liquid is ejected from the vibratable member.

8. The method of claim 1, wherein the vibratable member includes a plurality of holes, and wherein the liquid delivered to the rear surface is sized sufficiently to cover at least some of the plurality of holes until dispensed.

9. The method of claim 1, wherein the vibratable member is vibrated at a frequency at about 20 kHz to 200 kHz to eject the liquid.

10. The method of claim 1, further comprising drawing the liquid delivered from the supply container to the rear surface by capillary action.

11. The method of claim 1, where the liquid is an insecticide and wherein the liquid is dispensed at a rate in the range from about 0.5 cm$^3$ to 2 cm$^3$ per hour.

12. The method of claim 11, wherein the liquid is ejected from the front surface in droplets having a mean size in the range from 3 $\mu$m to 10 $\mu$m.

13. The method of claim 1, where the liquid is an air freshener and wherein the liquid is dispensed at a rate in the range from 1 cm$^3$ to 2 cm$^3$ per hour.

14. The method of claim 13, wherein the liquid is ejected from the front surface in droplets having a mean size in the range from 3 $\mu$m to 10 $\mu$m.

15. An apparatus for dispensing liquid as an atomized spray, comprising:

a vibratable member having a front surface, a rear surface, and at least one tapered hole extending therebetween, the tapered hole having a larger cross sectional area at the rear surface than at the front surface;

a vibrator to vibrate the vibratable member;

a supply container for holding the liquid to be dispensed;

a delivery system to deliver the liquid from the supply container and to the rear surface of the vibratable member in limited volumes so that the volumes delivered adhere to the rear surface of the vibratable member by surface tension contact; and a flow regulator for regulating the flow of the liquid from the container and to the rear surface of the vibratable member, the flow regulator allowing for delivery of the liquid in volumes that are substantially equal to the volumes dispensed from the hole in the vibratable member.

16. The apparatus of claim 15, wherein the flow regulator includes a gas vent in fluid communication with the supply container for allowing gas to flow into the supply container in volumes that are sufficient to replace the volumes that are delivered to the rear surface.

17. The apparatus of claim 16, wherein the gas vent is closed when filled with liquid from the supply container and is opened upon transfer of liquid from the gas vent to replace liquid ejected from the vibratable member upon vibration of the vibratable member.

18. The apparatus of claim 17, wherein the means for delivery includes a fluid path extending from the supply container, and wherein the gas vent is in communication with the fluid path.

19. The apparatus of claim 18, wherein the delivery system further comprises a capillary channel in the fluid path.

20. The apparatus of claim 15, wherein the flow regulator regulates the flow of the liquid to the vibratable member at a rate that is substantially equal to the rate of liquid dispensed from the hole.

21. The apparatus of claim 16, wherein the gas vent is distanced from the supply container at a distance sufficient to allow the liquid to be delivered to the rear surface at a rate that is substantially equal to the rate of liquid dispensed from the hole.

22. The apparatus of claim 16, wherein the supply container is at a higher elevation than the gas vent.

23. The apparatus of claim 15, wherein the vibratable member includes a plurality of holes.

24. An apparatus for dispensing liquid as an atomized spray, comprising:

a housing having an ejection port;

a vibratable member within the housing, the vibratable member having a front surface, a rear surface, and at least one tapered hole extending therebetween, the tapered hole having a larger cross sectional area at the rear surface than at the front surface, the tapered hole being aligned with the ejection port;

a delivery system to deliver liquid to the rear surface of the vibratable member in limited volumes so that the volumes delivered adhere to the rear surface by surface tension contact; and a vibrator in the housing for vibrating the member to elect the liquid through the tapered hole.

25. The apparatus of claim 24, further comprising a liquid supply container connected to the housing for holding the liquid to be dispensed.

26. The apparatus of claim 25, further comprising a flow regulator for regulating the flow of the liquid from the container and to the vibratable member, the flow regulator allowing for delivery of the liquid in volumes that are substantially equal to the volumes dispensed from the hole in the vibratable member.

27. The apparatus of claim 26, wherein the flow regulator regulates the flow of the liquid to the vibratable member at a rate that is substantially equal to the rate of liquid dispensed from the hole.

28. The apparatus of claim 24, wherein the vibrator comprises an ultrasonic transducer powered by a battery.

29. The apparatus of claim 28, further comprising a controller within the housing for controlling actuation of the transducer.

30. The apparatus of claim 29, wherein the controller is preprogrammed to cyclically actuate the transducer.

31. The apparatus of claim 26, wherein the supply container is elevated above the flow regulator.

* * * * *